(12) United States Patent
Adelung et al.

(10) Patent No.: US 9,182,399 B2
(45) Date of Patent: Nov. 10, 2015

(54) VIRUS TRAPS

(75) Inventors: Rainer Adelung, Kiel (DE); Yogendra Kumar Mishra, Kiel (DE); Claudia Röhl, Preetz (DE); Deepak Shukla, Orland Park, IL (US); Frank Spors, Rancho Cucamonga, CA (US); Vaibhav Tiwari, Westmont, IL (US)

(73) Assignees: Christian-Albrechts-Universitaet Zu Kiel, Kiel (DE); Universitatsklinikum Schleswig-Holsten, Kiel (DE); Western University of Health Sciences, Pomona, CA (US); The Board of Trustees of the University of Illinois, Urbana, IL (US)

( * ) Notice: Subject to any disclaimer, the term of this patent is extended or adjusted under 35 U.S.C. 154(b) by 198 days.

(21) Appl. No.: 13/593,934

(22) Filed: Aug. 24, 2012

(65) Prior Publication Data

US 2014/0056947 A1 Feb. 27, 2014

(51) Int. Cl.

| | |
|---|---|
| *A61K 9/14* | (2006.01) |
| *A61P 31/12* | (2006.01) |
| *B01L 99/00* | (2010.01) |
| *C12N 11/00* | (2006.01) |
| *G01N 33/569* | (2006.01) |
| *A61K 33/30* | (2006.01) |
| *A61K 47/48* | (2006.01) |

(52) U.S. Cl.

CPC .......... *G01N 33/56988* (2013.01); *A61K 33/30* (2013.01); *A61K 47/48861* (2013.01)

(58) Field of Classification Search

None

See application file for complete search history.

(56) References Cited

U.S. PATENT DOCUMENTS

| | | | | |
|---|---|---|---|---|
| 5,208,031 A * | 5/1993 | Kelly | ........................... | 424/412 |
| 6,730,329 B1 * | 5/2004 | Smith | ........................... | 424/642 |

FOREIGN PATENT DOCUMENTS

WO 2011/116751 A2 9/2011

OTHER PUBLICATIONS

Li, Applications for Nanomaterials in Critical Technologies, University of Illinois at Urbana Champaign, 2010.*
Dai, Chemical Physics Letters, 358, 2002.*
Feng, JACS, 126, 2004.*
Yoon, Materials Research Bulletin, 35, 2000.*
Wille, SPIE, Dec. 5, 2011.*
Akhtar, et al., 2009. Viral entry mechanisms: cellular and viral mediators of herpes simplex virus entry. FEBS J. 276, 7228-7236. 454.
Baram-Pinto, et al., 2010. Inhibition of HSV-1 attachment, entry, and cell-to-cell spread by functionalized multivalent gold nanoparticles. Small 6(9), 1044-1050.
Beasley, et al., 2010. Characterization of the UVA protection provided by avobenzone, zinc oxide, and titanium dioxide in broad-spectrum sunscreen products. Am J Clin Dermatol. 11, 413-421.
Bowman, et al., 2008.Inhibition of HIV fusion with multivalent gold nanoparticles. J Am Chem Soc. 130(22), 6896-6897.
Burgos, et al., 2008. Zebrafish as a new model for herpes simplex virus type-1 infection.Zebrafish 5, 323-333.
Corey, et al., 1986. Infections with herpes simplex viruses. N. Eng. J. Med. 314, 686-691.
Dambrosi, et al., 2010.Neurovirulence and latency of drug-resistant clinical herpes simplex viruses in animal models. J. Med. Virol. 82, 1000-1010.
Dean, et al., 1994. Single amino acid substitutions in gD of herpes simplex virus 1 confer resistant to gD-mediated interference and cause cell type-dependent alterations in infectivity. Virology 199, 67-80. 474 interference.
Desai, et al., 1998. Incorporation of the green fluorescent protein into the herpes simplex virus type 1 capsid. J. Virol. 72, 7563-7568.
Hill, et al., 2008. The high prevalence of herpes simplex virus type 1 DNA in human trigeminal ganglia is not a function of age or gender. J. Virol. 85, 8230-8234.
Kachynski, et al., 2008.Zinc Oxide Nanocrystals for Non-resonant Nonlinear Optical Microscopy in Biology and Medicine. J Phys Chem C Nanomater Interfaces. 112, 10721-10724.
Kaye, et al., 2000.Human herpesviruses in the cornea. Br. J. Opthalmol. 84, 563-571.
Kong, et al., 2008.Dominant ultraviolet light emissions in packed ZnO columnar homojunction diodes Appl. Phys. Lett. 93, 132113.
Lara, et al., 2010. Mode of antiviral action of silver nanoparticles against HIV-1. J Nanobiotechnology. 20;8:1. Liesegang, T.J., 2001. Herpes simplex virus epidemiology and ocular importance. Cornea 20, 1-13.
Liesegang, T.J., 2001. Herpes simplex virus epidemiology and ocular importance. Cornea 20, 1-13.
Lowry, et al., 1951 J. Biol. Chem. 193, 265-275.
Montgomery, et al., Herpes Simplex Virus-1 Entry into Cells Mediated by a Novel Member of the TNF/NGF Receptor Family. Cell. 1996;87(3):427-436.
Mosmann, T., 1983. Rapid colorimetric assay for cellular growth and survival: Application to proliferation and cytotoxicity assays. J. Immunological Methods 65, 55-63.
Rasmussen, et al., 2010. Zinc oxide nanoparticles for selective destruction of tumor cells and potential for drug delivery applications. Expert Opin Drug Deliv. 9, 1063-1077.
Roehl, et al., 2005. Microglia is activated by astrocytes in trimethyltin intoxication. Toxicology and Applied Pharmacology 204, 36-45.

(Continued)

*Primary Examiner* — Susan Tran
*Assistant Examiner* — William Craigo
(74) *Attorney, Agent, or Firm* — Meunier Carlin & Curfman LLC

(57) ABSTRACT

Specific applications of particles and particle agglomerates with semiconductor surfaces are provided. The particles and particle agglomerates display a high affinity for viral particles, and may be used therapeutically and/or prophylactically to treat or prevent viral infections. The particles and particle agglomerates may also be used to remove viral particles from a surface or fluid, e.g., as an absorbent in a filter, applied to surfaces to render them virostatic, and as tool to handle viral particles, e.g., for research, diagnostic, or decontamination purposes.

17 Claims, 7 Drawing Sheets

(56) References Cited

OTHER PUBLICATIONS

Schulte, et al., 2010. Acyclovir resistance in herpes simplex encephalitis. Ann Neurol. 67, 830-833.

Shukla, et al., 1999. A novel role for 3-O-sulfated heparan sulfate in herpes simplex virus 1 entry. Cell 99, 13-22.

Superti, et al., 2008.New advances in anti-HSV chemotherapy.Curr Med Chem. 15, 900-911.

Tallury, et al., 2010.Nanobioimaging and sensing of infectious diseases.Adv Drug Deliv Rev. 62(4-5):424-37.

Tiwari, et al., 2004. A role for 3-Osulfated heparin sulfate in cell fusion induced by herpes simplex virus type 1. J. Gen. Virol. 85, 805-809.

Tiwari, et al., 2006. Role for 3-O-sulfated heparan sulfate as the receptor for herpes simplex virus type 1 entry into primary human corneal fibroblasts. J. Virol. 80, 8970-8980.

Travan, et al., 2010. Silver-polysaccharide nanocomposite antimicrobial coatings for methacrylic thermosets. Acta Biomater. [Epub ahead of print].

Vig, et al., 2008. Use of Nanoparticles as Therapy for Respiratory Syncytial Virus Inhibition. Nanotechnology 2008: Life Sciences, Medicine & Bio Materials—Technical Proceedings of the 2008 NSTI Nanotechnology Conference and Trade Show, vol. 2 :543-546.

Whitley, et al., 1998. Herpes simplex viruses. Clin. Infect. Dis. 26, 541-553.

Wu, et al., 2011. Ultraviolet-Light-Assisted Formation of ZnONanowires in Ambient Air: Comparison of Photoresponsive and Photocatalytic Activities in Zinc Hydroxide. The Journal of Physical Chemistry 115 (5), pp. 2235-2243.

Mishra et al., Virostatic potential of micro—nano filopodia-like ZnO structures against herpes simplex virus-1, Antiviral Research, 92:305-312 (2011).

\* cited by examiner

VIRUS TRAPS

FIELD OF THE INVENTION

The present invention relates to the use of particles or particle agglomerates with semiconductor surfaces as a viral particle binding substrate.

BACKGROUND

Viral infections are a major threat in the modern world and new solutions are urgently required to deal effectively with this global concern.

Herpes simplex virus type-1 (HSV-1) infections are extremely widespread in the human population. The virus causes a broad range of diseases ranging from labial herpes, ocular keratitis, genital disease and encephalitis (Whitley et al., 1998; Corey and Spear, 1986). The herpetic infection is a major cause of morbidity especially in immunocompromised patients. Following initial infection in epithelial cells, the HSV establishes latency in the host sensory nerve ganglia (Akhtar and Shukla, 2009; Hill et al., 2008). The virus emerges sporadically from latency and causes lesions on mucosal epithelium, skin, and the cornea, among other locations. Prolonged or multiple recurrent episodes of corneal infections can result in vision impairment or blindness, due to the development of herpetic stromal keratitis (HSK) (Kaye et al., 2000). HSK accounts for 20-48% of all recurrent ocular HSV infections leading to significant vision loss (Liesegang, 2001). HSV infection may also lead to other diseases including retinitis, meningitis, and encephalitis (Corey and Spear, 1986).

The development of novel strategies to eradicate herpes simplex virus (HSV) is a global public health priority (Superti et al., 2008). While acyclovir and related nucleoside analogs provide successful modalities for treatment and suppression, HSV remains highly prevalent worldwide. The emergence of acyclovir-resistant virus strains, ability of virus to uniformly establish latency coupled with adverse effects of available anti-herpetic compounds provides a stimulus for increased search for new effective antiviral agents that target additional steps in viral pathogenesis such as cell entry (Schulte et al., 2010; Dambrosi et al., 2010). In addition, the current available treatments are unable to destroy HSV completely and therefore the virus remains dormant and keeps being active from time to time to cause various clinical manifestations. Therefore, there is great need to find suitable biocompatible, multifunctional, and low dimensional (scale lengths comparable to viruses) inorganic/organic agents which work to neutralize the virus infectivity, destabilize and possibly dismantle the virus particles. Recent developments in nanotechnology offer opportunities to re-explore biological properties of known antimicrobial compounds by manipulation of their sizes (Travan et al., 2010).

SUMMARY

Accordingly, provided are means for binding viral particles that may be used therapeutically and/or prophylactically and further as a tool to handle viral particles, e.g., for research or decontamination purposes.

Particles or particle agglomerates with semiconductor surfaces as viral particle binding substrates have been identified.

Provided are particles or particle agglomerates with semiconductor surfaces that may be used as viral particle binding substrates. The particles comprise polar defect sites, have an average surface to volume ratio larger than 7 for a unit volume and have a preferred largest cross sectional length in a range of from about 100 nm to about 30 μm.

The particles may be of the snowflake type, having for example the shape of tetrapods, interconnected hexagonal rods, or sea urchins capped with nanoscopic filopodia-like structures.

The particles may be synthesized for example by flame transport synthesis or by any other means known to those skilled in the art.

The particles or particle agglomerates may comprise a mixture of at least two semiconductor compounds.

In certain embodiments, the particles or particle agglomerates comprise zinc oxide (ZnO).

It has been determined that the cell toxicity of ZnO particles of this type is very low, toxicity only being observed well above the concentration ranges in which the particles are effective as virus binding substrate. ZnO particles also significantly block HSV-1 entry into glycoprotein D receptor expressing CHO-K1 cells. Moreover, ZnO particles significantly block HSV-1 entry into naturally susceptible cells. Furthermore, treatment with ZnO particles was shown to inhibit HSV-1 glycoprotein mediated cell-to-cell fusion and polykaryocytye formation. ZnO particles were shown to block viral entry for different clinically-relevant strains of HSV. ZnO particles were also shown to prophylactically block HSV infection in vivo, in the zebrafish embryo model.

The particles or particle agglomerates may have been doped to generate polar defect sites. The doping may occur directly before the use as a viral particle binding substrate, but it may also occur at another time before the use. The term doping used here includes the oxygen vacancy generation on the surface of the material.

Uses also extend to ZnO particles or particle agglomerates that have been doped to generate polar defect sites. Doping may occur for example by UV-treatment, by heating under $H_2$-atmosphere or by any other method known by those skilled in the art.

Pre-treatment of ZnO particles with UV illumination enhances anti-HSV-1 activity.

Uses extend to enveloped viral particles. These viral particles may be herpes simplex or human immunodeficiency viral particles or any other enveloped viral particles that bind to particles or particle agglomerates with semiconductor surfaces and comprising polar defect sites and that have the average surface to volume ratios and size characteristics described herein.

In one embodiment, a pharmaceutical composition for the treatment and prevention of conditions caused by viral infection is provided comprising particles or particle agglomerates with semiconductor surfaces comprising polar defect sites and that have average surface to volume ratios and size described herein. The pharmaceutical composition comprises particles or particle agglomerates as a viral particle binding substrate in physiologically effective doses in a pharmaceutically acceptable carrier.

In another embodiment, particles or particle agglomerates with semiconductor surfaces comprising polar defect sites and that have average surface to volume ratios and size characteristics described herein are used as viral particle binding substrates in the preparation of a medicament for the treatment and/or prophylaxis of conditions caused by viral infection.

Also provided is a method for binding viral particles present in a liquid, comprising applying to the viral particle containing liquid a composition comprising particles or particle agglomerates with semiconductor surfaces comprising polar defect sites and that have average surface to volume ratios and size characteristics as described herein as a viral particle binding substrate.

Also provided is a method for binding viral particles present on a surface, comprising applying to a liquid a composition comprising particles or particle agglomerates with semiconductor surfaces comprising polar defect sites and that have average surface to volume ratios and size characteristics as described herein as viral particle binding substrate, and putting that liquid in contact with the viral particle contaminated surface.

Also provided is a method for binding viral particles, comprising applying to a surface a composition comprising particles or particle agglomerates with semiconductor surfaces comprising polar defect sites and that have average surface to volume ratios and size characteristics as described herein, and putting that surface in contact with viral particles. The particles or particle agglomerates may suitably be formulated for application in an appropriate carrier, coating or solvent.

Also provided is a method for binding viral particles, comprising applying to a filter a composition comprising particles or particle agglomerates with semiconductor surfaces comprising polar defect sites and that have average surface to volume ratios and size characteristics as described herein, and putting the filter in contact with viral particles.

The filter may be a blood filter, or alternatively also a water or an air filter.

Also provided is a device for binding viral particles contained in fluids. Such a device may comprise particles or particle agglomerates with semiconductor surfaces comprising polar defect sites and that have average surface to volume ratios and size characteristics described herein as a viral particle binding substrate, further comprising a device for doping the particles or particle agglomerates to generate polar defect sites as well as a device for pumping fluids.

DESCRIPTION OF DRAWINGS

FIG. 3. Dosage response of ZnO semiconductor particles on the inhibition of HSV-1 entry into Chinese Hamster Ovary (CHO-K1) cells expressing gD receptor nectin-1.
(A) In this experiment, β-galactosidase-expressing recombinant virus HSV-1 (KOS) gL86 (25 pfu/cell) was pre-incubated with ZnO-SCPs at indicated concentrations (gray bars) or mock-incubated with 1×phosphate buffer saline (PBS; black bar) for 90 min at room temperature. The uninfected cells were used as negative control (white bar). After 90 min the virus was incubated with CHO-K1 cells expressing gD receptor nectin-1 expressing cells. After 6 h, the cells were washed, permeabilized and incubated with ONPG substrate (3.0 mg/ml) for quantitation of β-galactosidase activity expressed from the input viral genome. The enzymatic activity was measured at an optical density of 410 nm (OD $410_{nm}$). The value shown is the mean of three or more determinations (±SD).

(B) Dosage response of ZnO-SCPs on the inhibition of HSV-1 entry into natural target cells. Naturally susceptible human corneal fibroblasts (CF) were used in this experiment. The β-galactosidase-expressing recombinant virus HSV-1 (KOS) gL86 (25 pfu/cell) was pre-incubated with ZnO-SCPs at indicated concentrations (grey bars) or mock treated with 1×phosphate buffer saline (PBS) for 90 min at room temperature (black bar). The uninfected cells were used as negative control (white bar). After 90 min of ZnO-SCP treatment, the virus was incubated with CF cells. After 6 h, the cells were washed, permeabilized and incubated with ONPG substrate (3.0 mg/ml) for quantitation of β-galactosidase activity expressed from the input viral genome. The enzymatic activity was measured at an optical density of 410 nm (OD $410_{nm}$). Each value shown is the mean of three or more determinations (±SD).

FIG. 4. Effect of UV-illumination on ZnO semiconductor particles
(A-C) UV-illumination on ZnO-SCPs significantly enhances HSV-1 binding.
ZnO-SCPs were exposed to UV illumination for 30 min. SCPs were stained red via phalloidin treatment (A). UV-untreated (B) and UV-treated (C) ZnO-SCPs were mixed with green fluorescent protein (GFP)-tagged HSV-1 (VP26). The UV-exposed ZnO-SCPs show significant HSV-1 trapping as indicated by strong co-localization signal (highlighted by arrows) compared to UV-untreated ZnO-SCPs.

(D) Pre-incubation of UV-treated ZnO-SCPs with HSV-1 significantly blocks viral entry.
In this experiment, β-galactosidase-expressing recombinant virus HSV-1 (KOS)gL86 (25 pfu/cell) was pre-incubated for 90 min with the UV pre-treated (+) or untreated(−) ZnO-SCPs at 0.1 mg/ml. HSV-1 KOS gL86 mock-incubated with 1×phosphate buffer saline (PBS; black bar) was used as positive control. The uninfected cells were used as negative control (grey bar). After 90 min the soup was challenged to CF. After 6 h, the cells were washed, permeabilized and incubated with ONPG substrate (3.0 mg/ml) for quantitation of β-galactosidase activity expressed from the input viral genome. The enzymatic activity was measured at an optical density of 410 nm (OD $410_{nm}$). The value shown is the mean of three or more determinations (±SD).

FIG. 5. UV treated ZnO semiconductor particles significantly impair HSV-1 glycoproteins induced cell to cell fusion and polykaryocytes formation.
(A) The effector CHO-K1 cells expressing HSV-1 glycoproteins (gB, gD, gH-gL) along with T7 plasmid were preincubated with 100 μg/ml UV-treated ZnO-SCPs or with 1×PBS for 90 min. The two pools of effector cells (ZnO-SCPs treated and PBS treated) were mixed with target CHO-K1 cells expressing the luciferase gene along with the specific gD receptor nectin-1. Membrane fusion as a means of viral spread was detected by monitoring luciferase activity. Relative luciferase units (RLUs) were determined using a Sirius luminometer (Berthold detection systems). Black bars and grey bars represent 1×PBS treated and ZnO-SCPs treated cells, respectively. The effector cells devoid of HSV-1 glycoprotein mixed with target CHO-K1 nectin-1 expressing cells were used a negative control (white bar). Error bars represent standard deviations. ** $P<0.05$, one way ANOVA.

(B) Microscopic visualization of polykaryocyte impairments by ZnO-SCPs. In this experiment, effector CHO-K1 cells expressing four essential HSV-1 glycoproteins (gB, gD, gH-gL) were either pre-incubated with ZnO-SCPs or with 1×PBS for 90 min before they were co-cultured in 1:1 ratio with target nectin-1 expressing CHO-K1 cells for 24 h. The cells were fixed (2% formaldehyde and 0.2% glutaraldehyde) for 20 min and then stained with Giemesa stain (Fluka) for 20 min. Shown are photographs of representative cells pictured under microscope (Zeiss Axiovert 200) at 40× objective. The upper (a) panel shows no polykaryocyte formation in absence of HSV-1 glycoprotein (negative control), the middle panel (b) shows significant inhibition of polykaryocyte formation in presence of HSV-1 glycoprotein in effector cells fused with target nectin-1 CHO-K1 cells. The lower panel (c) shows no polykaryocyte formation in presence of ZnO-SCPs during co-culture of HSV-1 glycoprotein expressing cells with target nectin-1 expressing CHO-K1 cells.

(A) HSV-1 entry blocking activity of SCPs is viral-strain independent. In this experiment clinical strains of HSV (F, G, and MP at 25 pfu/cell) were either pre-incubated with 1×PBS (−) or with ZnO-SCPs(+) at 10 µg/ml for 90 min at room temperature. After 90 min of incubation the two pools of viruses were incubated on CHO Ig8 cells that express β-galactosidase upon viral entry. The viral entry blocking was measured by ONPG assay.

(B) ZnO-SCPs block HSV-1 infection in embryo model of zebrafish. In this experiment β-galactosidase expressing HSV-1 (KOS) gL86 reporter virus at $2 \times 10^8$ pfu were pre-incubated with 1×PBS (−) or with 100 µg/ml SCPs (+) for 2 hours before infecting zebrafish embryos for 12 h. HSV-1 entry in both the groups of embryos was measured by ONPG assay.

This scheme illustrates the three major steps (I-III) involved during HSV-1 entry. During step I, HSV-1 glycoprotein B (gB) binds to cell surface heparan sulfate (HS), subsequently in step II HSV-1 gD binds to any one of the cell surface receptors (nectin, HVEM and/or 3-O sulfated heparin sulfate) which results in virus-cell membrane fusion. Step III involves viral capsid trafficking via cytoplasm (Cy) to reach the nucleus (Nu) for viral DNA replication. Interaction of HSV-1 with ZnO-SCPs bearing spikes results in HSV-1 trapping, subsequently affecting early phases of virus-cell interactions and viral entry.

DETAILED DESCRIPTION

The use of functionalized nanoparticles to develop antiviral agents that act by interfering with viral infection, in particular attachment and entry is gaining wide popularity (Tallury et al., 2010; Bowman et al., 2008; Lara et al., 2010; Vig et al., 2008). These particles generally exhibit high surface to volume ratios, leading to entirely new properties as compared to the bulk form of the substance. For example, gold nanoparticles were shown to inhibit cell-to-cell spread of HSV (Baram-Pinto et al., 2010).

ZnO has long been known for its antibacterial and antifungal properties including the recent report for selective destruction of tumor cells by ZnO nanoparticles and its potential in the development of anti-cancer agents (Rasmussen et al., 2010). In addition, the use of ZnO nanoparticles in sunscreens is one of the most common uses of nanotechnology in consumer products (Beasley and Meyer, 2010). Recently the use of ZnO nanostructures has been suggested in nonresonant nonlinear optical microscopy in biology and medicine (Kachynski et al., 2008). WO 2007/093808 A1 is directed to the use of nanoparticles of metals and/or metal compounds, including ZnO in the prevention of viral infection.

There is a need in the art for efficient, well-tolerated and inexpensive agents for the treatment and/or prevention of conditions caused by viral infections.

Provided are specific applications of particles or particle agglomerates with semiconductor surfaces (semiconductor particles, SCPs) with polar defect sites that can be used as a viral particle binding substrate. The particles described herein have an average surface to volume ratio larger than 7 for a unit volume and have a preferred largest cross sectional length in a range of from about 100 nm to about 30 µm.

A significantly enlarged average surface to volume ratio for a unit volume (compared for example to less elaborate structures mainly with planar surfaces or to spherical particles), as described herein, offers an advantageous potentially large binding interface between SCPs and the viral particles. The SCPs may be of similar size to or of smaller or larger size than any given target viral particle.

SCPs with semiconductor surfaces comprising different metals (e.g. Zn, Sn, Fe, Bi, Al, In, Zr, Ti, Ni), metal-oxides (e.g. $ZnO$, $SnO_2$, $TiO_2$, $In_2O_3$, $Fe_2O_3$, $Bi_2O_3$, $Al_2O_3ZrO_2$), metal-sulphides, metal-nitrides and metal-carbides may be used for binding viral particles. Various combinations from the above mentioned metals such as for example Zn—Fe, In—Zn, Sn—Zn, In—Zn—Sn, In—Sn, Bi—Zn, Bi—Sn, Fe—Bi, Zn—Ti, Sn—Ti, In—Ti, etc. may also be used for binding viral particles. The particles or particle agglomerates may also comprise a mixture of at least two semiconductor compounds with polar defect sites.

Mass production of free standing SCPs using suitable synthesis techniques is one of the main requirements for their use in antiviral applications. One suitable method for the production of these SCPs is flame synthesis, described in WO 2011/116751 A2. This method enables the production of large amounts (kilograms) of metal, metal-oxide, metal-sulphide, metal-nitride or metal-carbide SCPs in a cost-effective manner.

The SCPs with an average surface to volume ratio larger than 7 for a unit volume may be of the snowflake type, having for example the shape of tetrapods, interconnected hexagonal rods, or sea urchins capped with nanoscopic filopodia-like structures. Such forms exhibit high surface to volume ratios for a unit volume as compared to their bulk counterparts, leading to advantageous functional properties such as efficient viral particle binding. The largest cross sectional length of such SCPs should be between about 100 nm and about 30 µm.

A general SCP form may be a core-spike/filopodia-type structure, i.e. a structure consisting of a core covered by spikes. Such a structure may have for example a metal or metal oxide core surrounded by spikes of metal oxide. The average diameter of the SCP core may vary in the range of 100 nm to 10 µm, depending on the powder characteristics initially used for synthesis. The dimensions of the spikes may also be controlled by varying synthesis conditions (mainly temperature and time). The diameter of the spikes may range from 20 nm to 4 µm, whereas their length may vary from 25 nm to 20 µm.

SCPs with these characteristics have the advantage of being self-supported, i.e. they do not require a substrate, and they can easily be handled for application.

The viral binding activity of the SCPs not only depends on their surface polarity but is also strongly influenced by the existing polar defects, both intrinsic defects (like grain boundaries, twin boundaries, vacancies/interstitials etc.) and extrinsic defects (external doping elements).

The particles or particle agglomerates may thus be doped to generate polar defect sites. Hence, metal, metal-oxide, metal-sulphide, metal-nitride, metal-carbide and/or mixed composition SCPs may be functionalized by suitable physical or chemical treatments to generate polar defect sites leading to the desired viral particle binding.

Metal-oxide (for example ZnO, $TiO_2$, etc.) and/or metal-sulphide SCPs may be illuminated with ultraviolet (UV) light to generate polar defect sites. UV illumination results in the creation of electron-hole pairs (depending on the bandgap) which results in changes in surface polarities by creating oxygen vacancies in metal-oxide SCPs. In particular, ZnO-SCPs may be doped to generate polar defect sites for example by UV-treatment or by heating under $H_2$-atmosphere.

Aging effects should be considered in this context: If the UV-treated metal-oxide SCPs remain in the dark for some time (for example a few days), oxygen in the atmosphere starts occupying the oxygen vacancies, thus neutralizing the polar defect sites. The doping may therefore occur directly before the use of the SCPs as a viral particle binding substrate, but it may also occur at another time before the use, taking these aging effects into account.

Common commercially available UV lamps may be used for SCP illumination. However, since the penetration depth of UV radiation is not very large (less than a few mm), the illumination conditions should be chosen so as to enable an efficient generation of polar defect sites.

SCPs according may be used to bind enveloped viral particles. These viral particles may be herpes simplex or human immunodeficiency viral particles or any other enveloped viral particles that bind to SCPs. These viral particles may thus for example be from the following groups:
1. DNA viruses
   1.1. Herpesviridae
      1.1.1. Alpha
      1.1.2. Beta
      1.1.3. Gamma
   1.2. Pox viridae
      1.2.1. Ortho
         1.2.2. Para
      1.2.3. Other
   1.3. Papillomaviridae
   1.4. Parvoviridae
2. RNA viruses
   2.1. Paramyxoviridae
   2.2. Togaviridae
   2.3. Picornaviridae
   2.4. Retroviridae SCPs may be part of a pharmaceutical composition for the treatment and/or prevention of conditions caused by viral infection. Such pharmaceutical compositions may contain particles or particle agglomerates in physiologically effective doses in a pharmaceutically acceptable carrier. In particular, ZnO-SCPs are effective at low concentrations (0.1-10 µg/ml) and only exhibit cytotoxic effects at higher concentrations (above 500 µg/ml).

Such SCPs may thus be used in the preparation of a medicament for the treatment and/or prophylaxis of conditions caused by viral infection. This medicament may be used topically in form of suspensions, ointments, creams, lotions and/or lipsticks.

The binding (and removal) of viral particles present in a liquid may be achieved by applying to the viral particle containing liquid a composition comprising the disclosed particles or particle agglomerates. The SCPs with bound viral particles may then be removed from the liquid by any method known in the art such as filtration, centrifugation, etc.

Moreover, viral particles present on a surface may be bound (and removed from the surface) by applying to a liquid a composition comprising particles or particle agglomerates as viral particle binding substrate, and putting that liquid in contact with the viral particle contaminated surface. Such SCP containing liquids may thus be used to wash surfaces and objects that should be freed from viral particles.

Also provided are methods for binding viral particles, wherein a composition comprising SCPs is applied to a surface, and this substrate surface is put contact with viral particles to enable binding. SCPs used in this method may suitably be formulated for application in an appropriate carrier, coating or solvent. SCPs may thus also for example be applied on conventional clinical tapes used for dressing wounds and lesions caused by viral infection.

Binding characteristics of SCPs further enable the generation of filters to trap viral particles. Such filters may consist of a free-standing interconnected stable network of SCPs or alternatively of a filter scaffold onto which the SCPs are applied.

Hence, also provided is a method for binding viral particles by applying to a filter a composition comprising SCPs, and putting the filter in contact with viral particles. Such a filter may be used to bind viral particles present in fluids as for example in viral particle contaminated water, in solutions, in culture media or in body fluids such as blood or also in the air. Decontamination procedures or viral research may thus be additional uses of SCPs.

Also provided is a device for binding viral particles contained in fluids. Such a device includes an SCP-based filter for viral particles with the possibility to treat the SCPs so as to generate polar defect sites, as well as a pump mechanism to enable fluid circulation through the filter and the device in general.

Generation of ZnO-SCPs and Cell Toxicity

Figure 1:
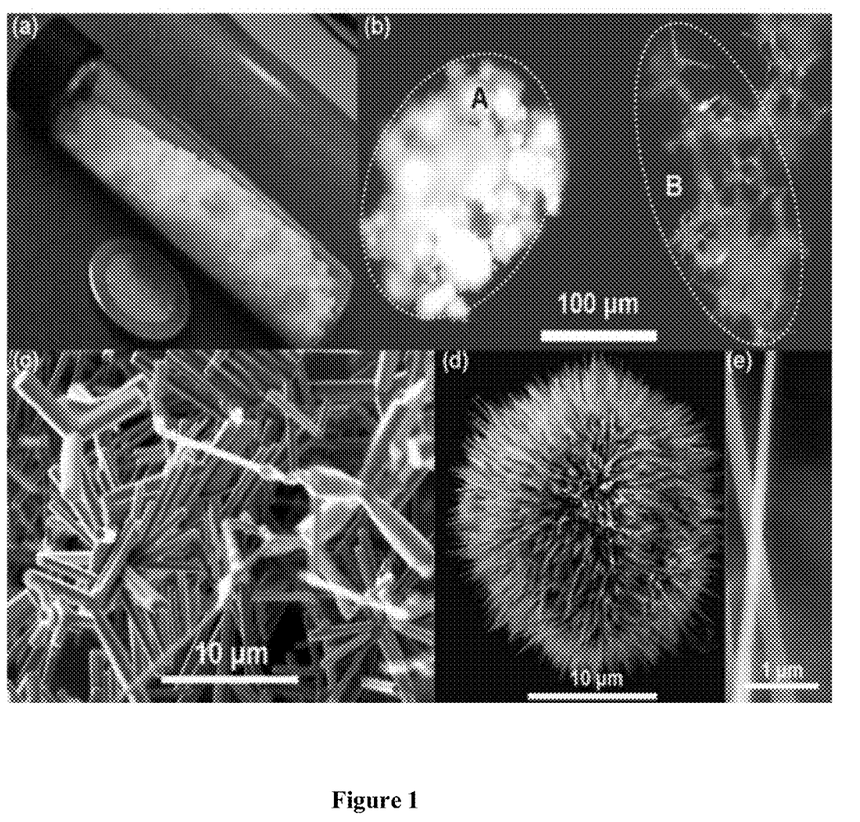
FIG. 1. ZnO semiconductor particles (SCPs).
(a) Synthesis of the ZnO-SCPs can be done in large quantities: image of synthesized ZnO-SCPs next to a 23 mm diameter coin.
(b) Microscope image comparing a standard powder (A) and the synthesized ZnO-SCPs (B).
(c) Electron micrograph showing the complex geometries.
(d) The powder contains a larger quantity of filopodia-like structures, which have spikes down to the nanoscale (e).

The large quantities (several 100 grams) of snowflake type ZnO-SCPs (tetrapods, interconnected hexagonal rods, sea urchins capped with nanoscopic filopodia-like structures) were synthesized by flame transport synthesis. The synthesized snowflake type ZnO powder stored in a glass tube is shown in FIG. 1a. Compared to standard powder (FIG. 1bA), the synthesized ZnO powder shows a higher order of tetrapod structures and a snowflake-like symmetry (FIG. 1bB). Scanning electron microscopy (SEM) (FIG. 1c) shows the geometric orientation and morphology of the semiconductor particles powder. A typical cluster of ZnO-SCPs can form a well-ordered array of sea urchin-like structures with filopodia-type nanospikes (FIG. 1d). Further analysis of the latter by SEM revealed that lengths of the spikes are in the range of a few microns (2 to 8 µm), with thicknesses ranging from 100 to 200 nm (FIG. 1e).

Figure 2:
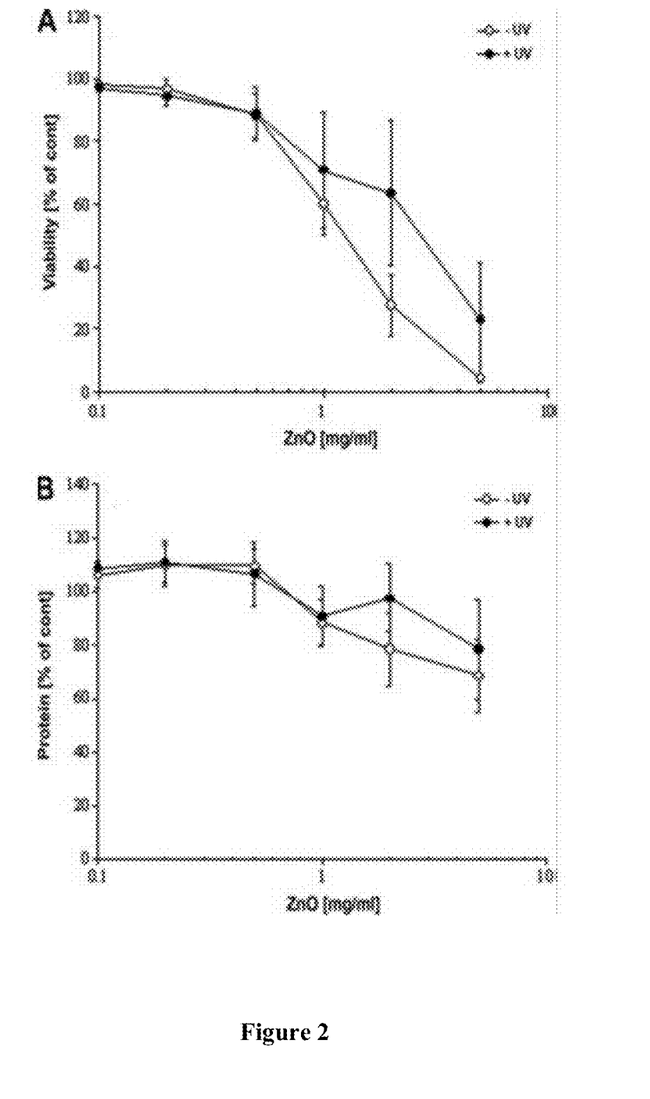
FIG. 2. Effect of ZnO semiconductor particles on cell viability.
MTT assay (A) and total cell protein (Lowry assay; B) of human dermal fibroblasts after 24 h treatment with ZnO-SCPs that were either treated (+) or untreated (−) with UV light for one hour. Each data point represents the mean±SE of n=3 independent experiments.

Cell toxicity of the ZnO-SCPs was determined using human dermal fibroblasts (NHDF; PromoCell, C-12300). In terms of fibroblast viability, there is a clear concentration dependency of ZnO-SCPs toxicity (FIG. 2a). Concentrations up to 500 µg/ml do not significantly impair cell viability. The concentration-effect curve for ZnO-SCPs treated with UV-light is slightly shifted to the right. The EC50 value derived from the curves increases approximately twofold after UV-light treatment from about 1.3 to 3 mg/ml ZnO. Though this shift was statistically not significant, the results show that the toxicity of ZnO-SCP is not increased by UV treatment. Upon ZnO-SCP treatment, there is only a slight concentration-dependent decrease in total protein in cell cultures (FIG. 2b). This could be explained by the fact that, especially at higher concentrations, a layer of ZnO structures covers the cell monolayer, and this might have prevented in part the detachment of dead cells upon washing. The concentration of ZnO-SCPs was kept below the toxic levels throughout the following experiments.

Figure 3:
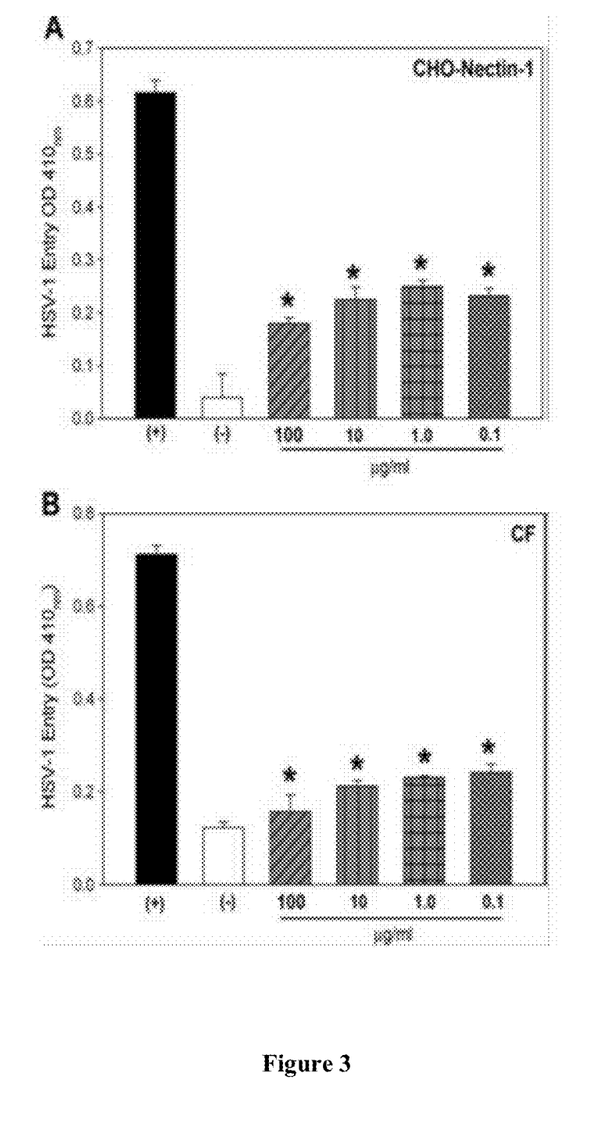

ZnO-SCPs Significantly Block HSV-1 Entry into Glycoprotein D (gD) Receptor Expressing CHO-K1 Cells The effect of ZnO-SCPs on HSV-1 entry into the target cells was determined by using β-galactosidase expressing HSV-1 reporter virus (gL86) into wild type Chinese hamster ovary (CHO-K1) cells expressing gD receptor nectin-1. As shown in FIG. 3A, HSV-1 pre-incubation with ZnO-SCPs significantly blocks viral entry in a dose dependent manner in CHO-K1 cells expressing gD receptors. The positive control cells treated with 1×PBS (untreated) showed HSV-1 entry. The blocking activity of ZnO-SCPs was pronounced even at low concentrations (0.1 µg/ml or 100 µg/ml).

ZnO-SCPs Significantly Block HSV-1 Entry into Naturally Susceptible Cells

Human corneal fibroblasts (CF), a natural target for HSV-1 infection, were used to further confirm the blocking activity of ZnO-SCPs on HSV-1 entry. CF express HVEM and 3-OST-3 as gD receptors (Tiwari et al., 2006). As shown in FIG. 3 (B), treatment with ZnO-SCPs (0.1 µg/ml or 100 µg/ml) leads to a significant blocking of HSV-1 entry. Similar results were obtained with HeLa cells that express all the known gD-receptors (data not shown). In all cases, the mock treated cells used as positive control showed HSV-1 entry. The results obtained with CF and HeLa cells are thus consistent with the results from nectin-1 expressing CHO-K1 cells: in all three in vitro systems, ZnO-SCPs at concentrations at least as low as 0.1 µg/ml significantly inhibit HSV-1 entry.

Pre-treatment of ZnO-SCPs with UV Illumination Enhances Anti-HSV-1 Activity

Figure 4:
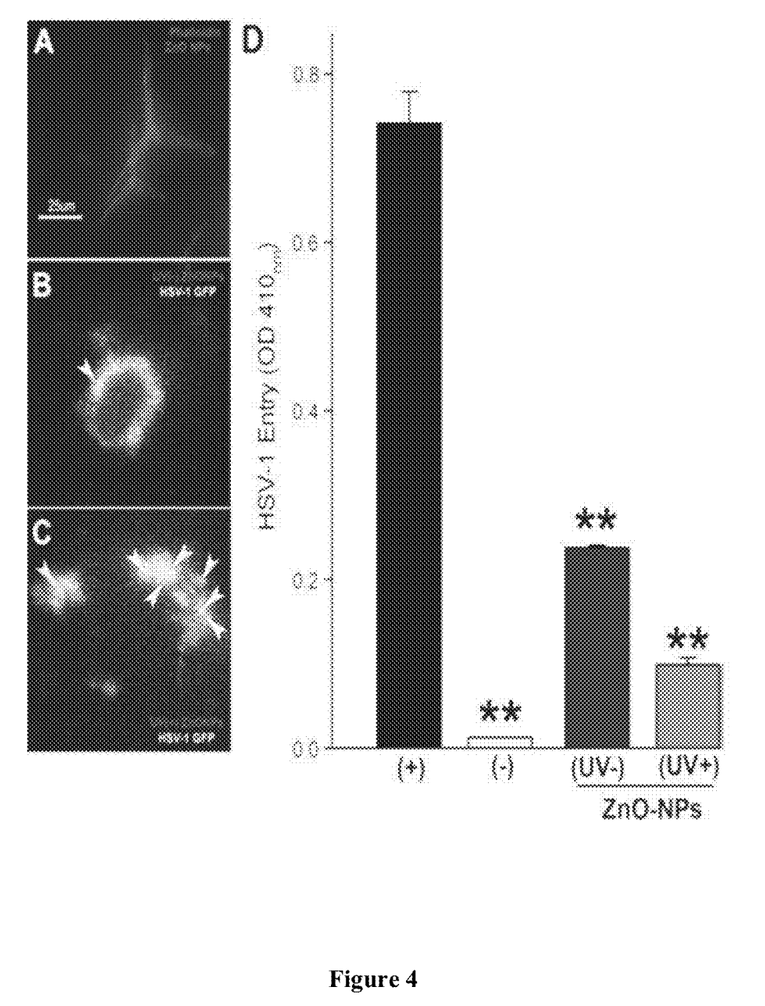

Assuming that viral entry inhibition properties of ZnO-SCPs are due to their partial negatively charged oxygen vacancies, ZnO-SCPs were exposed to UV illumination (Raytech UV-Lamp model R5-FLS-2; Midtown, Conn., USA) for 30 min, which is known to generate additional oxygen vacancies and hence additional negative charge centers on the atomic scale at the surface (Wu and Chen, 2011; Kong et al., 2008). In order to visualize the effect of UV illumination of ZnO-SCPs on viral binding, the SCPs were stained red via phalloidin staining (FIG. 4A). The UV treated red ZnO-SCPs were mixed with green fluorescent protein (GFP)-tagged HSV-1 (VP26). As shown in FIG. 4C, UV-exposed ZnO-SCPs (0.1 mg/ml) showed a significant viral trapping as evident by strong yellow co-localization signal as compared to UV-untreated red ZnO-SCPs (FIG. 4B). Enhanced viral trapping by UV-exposed ZnO-SCPs also translates into enhanced viral inhibition: HSV-1 (KOS) virions were pre-incubated with either UV-treated ZnO-SCPs or UV-untreated ZnO-SCPs before infecting target cells. Clearly, the UV-exposed particles were more efficient in blocking HSV-1 entry (FIG. 4D). This result underlines the significance of negative charged molecules in HSV-1 entry.

ZnO-SCP Treatment Inhibits HSV-1 Glycoprotein Mediated Cell-to-Cell Fusion and Polykaryocyte Formation Finally, the effect of ZnO-SCPs during HSV-1 glycoproteins mediated cell to cell fusion was investigated. The main emphasis of cell to cell fusion was to demonstrate the viral and cellular requirements during virus-cell interactions and also as means of testing viral spread. The goal was to determine whether ZnO-SCPs interaction with HSV-1 envelope glycoproteins, essential for viral entry, affects cell to cell fusion.

Figure 5:
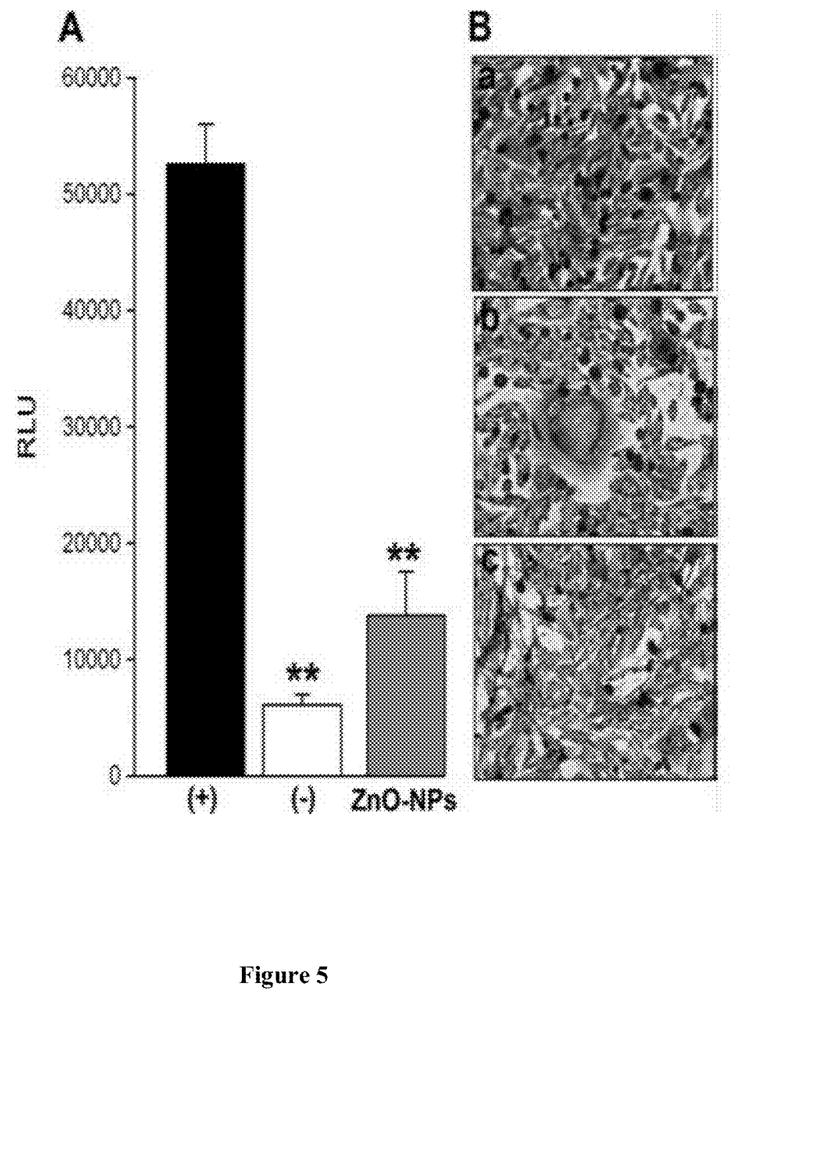

Surprisingly, ZnO-SCPs treatment (0.1 mg/ml) of effector cells expressing HSV-1 glycoproteins impaired cell to cell fusion in CHO-K1 cells expressing gD receptor nectin-1 (FIG. 5). In parallel, the control untreated effector cells co-cultured with target cells showed the expected fusion (FIG. 5; black bars in panel A). This response was further confirmed when polykaryocytes formation was visualized. ZnO-SCPs treated effector cells failed to form polykaryons when co-cultured with target cells (FIG. 5B; panel c). The control untreated effector cells efficiently showed larger polykaryons (FIG. 5B; panel b), while no polykaryons were observed in absence of HSV-1 glycoprotein (negative control, FIG. 5B; panel a). These results indicate that the presence of ZnO-SCPs significantly reduce viral penetration. ZnO-SCPs may therefore possibly disrupt the viral envelope glycoproteins binding to cell surface HS, thereby preventing the virus attachment, surfing, and fusion processes.

Clinical and In Vivo Significance of ZnO-SCPs Against HSV-1 Entry.

Figure 6:
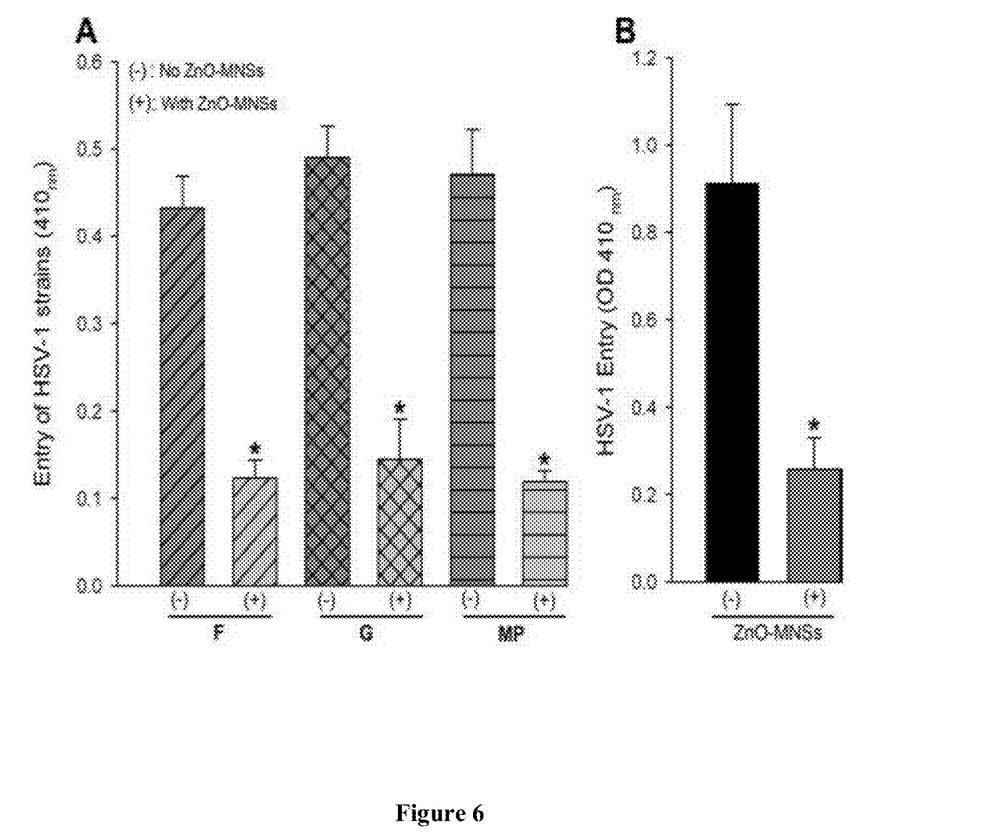
FIG. 6. Significance of ZnO-SCPs as anti-HSV agent.

To evaluate the broader significance of UV-treated ZnO-SCPs as an anti-HSV agent, the ability of SCPs to block viral entry for different clinically-relevant strains of HSV (F, G, and MP) (Dean et al., 1994) was tested. Here, nectin-1 expressing CHO Ig8 cells that express β-galactosidase upon viral entry (Montgomery et al., 1996) were used. The virulent strains were pre-incubated with SCPs, and then used for infecting the cells. The results from this experiment again showed that SCPs blocked entry of additional HSV strains as evident by ONPG assay (FIG. 6; panel A). Finally, the in vivo significance of SCPs in an animal model was addressed. For this zebrafish embryos were chosen, since these provide a quick and easy model for testing HSV-1 infection in vivo (Burgos et al., 2008). As shown in FIG. 6, panel B, the SCPs were able to prophylactically block infection of the zebrafish embryos as well. This result underlines the promising character of SCPs for the development of effective anti-HSV prophylactic agents.

The initial quantitative viral entry assay revealed that pre-treatment of HSV-1 with ZnO-SCPs significantly affected the viral entry at non-toxic concentrations (FIG. 3). UV-irradiated ZnO-SCPs were even more potent in blocking HSV-1 entry and spread. Fluorescent imaging experiments further confirmed the quantitative viral entry data that UV-treated ZnO-SCPs neutralized the viral infectivity by "viral-trapping" or "virostatic activity", which was evident from the enhanced accumulation of GFP-tagged virus around SCPs (FIG. 4). The viral trapping activity of SCPs can be explained as UV-exposure of ZnO spikes enhances the distribution of negative charge by oxygen vacancies, thereby allowing more viruses to bind.

The major advantage of ZnO-SCPs is their effectiveness at lower concentrations (µg), the low cost of their synthesis, molecular specificity to viral envelope protein without affecting the expression of native heparan sulfate chains, and ease in designing particle capsules coated with additional anti-HSV-1 agents including envelop glycoprotein B (gB) and D (gD) based peptides to block HSV-1 entry receptors while keeping the HSV-1 virions trapped to SCPs. ZnO is an integral component of skin, face and lip creams where HSV-1 infection or reactivation leads to painful blisters. Therefore ZnO-SCPs exhibit strong potentials to develop anti-HSV medication for cold sore in the form of a protective gel or cream, which may be further activated by UV-light, also by the UV portion of sun light. In addition, such SCPs will become the bench tool to create additional antiviral agents against many other viruses with the conjugation of peptides against specific virus envelope glycoproteins. Furthermore, they can also be used to deliver antiviral peptides with minimal pharmacokinetic problems together with enhanced activity of drug for the treatment of HSV infection.

Figure 7:
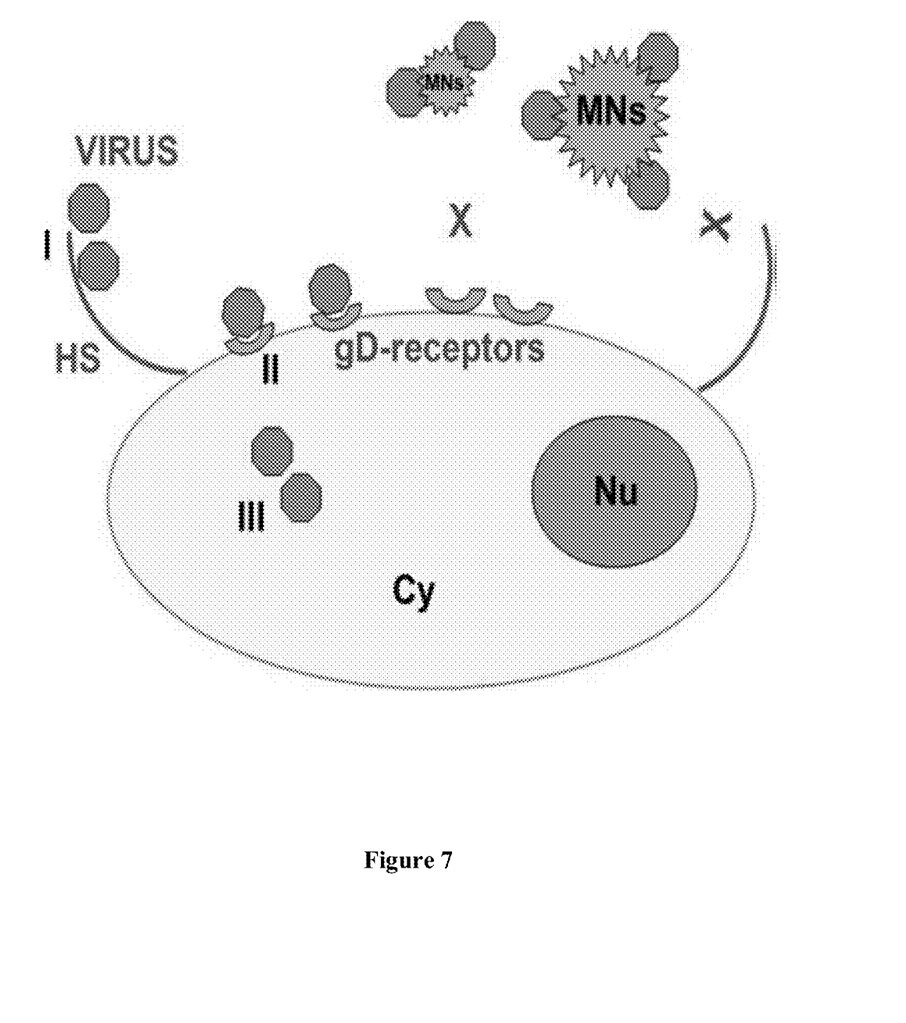
FIG. 7. Model for the ZnO semiconductor particles based HSV-1 inhibition.

Taken together the findings of the inventors support the model by which partially negatively charged ZnO-SCPs trap HSV-1 to prevent virus-cell interaction (FIG. 7), which are key steps for successful viral infection of the host cells and, therefore, SCPs-based compounds present a useful therapeutic approach. This is further supported by the observation that SCPs also block infection in vivo, in a zebra-fish model of HSV-1 infection (FIG. 6B).

The following examples are intended to illustrate the present invention but not to limit the scope thereof.

Example 1

Preparation and Characterization of Spikes Containing ZnO Semiconductor Particles The snowflake type free standing complex network of interconnected zinc oxide semiconductor particles (thickness in the range of 100 to 500 nm and length in the range of 1 to 5 μm) which consists of hexagonal nanorods, tetrapods, nanocombs and nano-sea-urchin-like structures, were synthesized by a simple flame transport synthesis approach using a sacrificial polymer (polyvinyl butyrol) as the local host. Commercial Zn powder(particle diameter ~3 to 5 μm; Goodfellows, UK) and polyvinyl butyrol powder (PVB; Kuraray Europe GmbH, Germany). The Zn and PVB powders were mixed in particular ratio with the help of ethanol and then heated in a simple furnace at 900° C. for 1 hour. The process for semiconductor particle formation was used as previously described (WO 2011/116751 A2). The microstructural evolution of different semiconductor particles inside snowflake type free standing powdery material was investigated by scanning electron microscopy (SEM) using a Philips XL-30 microscope equipped with LaB6 filament and energy dispersive X-ray diffraction analysis (EDAX) detector. SEM images of different structures were recorded at 6 kV electron beam acceleration voltage with 20 μA beam current. A large quantity of snowflake type ZnO semiconductor particle powder was synthesized under identical conditions and used for different biomedical tests, as described in the next examples.

Example 2

Cytotoxic Assay

The cytotoxicity of the ZnO-SCPs after 24 h of treatment was determined by MTT assay (Mosmann, 1983; Röhl and Sievers, 2005) and protein measurement (Lowry et al., 1951). After two days in culture, when confluence was reached, human fibroblasts (NHDF; PromoCell, C-12300) were treated with ZnO-SCPs. These were either first irradiated with UV light at 254 nm for one hour distributed in a thin layer in a plastic Petri dish or they were directly brought into suspension with culture medium at a concentration of 5 mg/ml. This stock solution was used to prepare the samples. For the treatment culture medium was completely removed and cells were treated with 0, 0.1, 0.2, 0.5, 1.0, 2.0, and 5.0 mg/ml ZnO-SCPs (−/+UV) for 24 h. Cells were washed carefully one time with the culture medium before using MTT assay or three times with phosphate-buffered saline(PBS) before the protein measurement. Using the MTT assay, the portion of viable cells in treated cultures was estimated on the basis of the formation of formazan by viable cells. Formazan and protein suspensions were transferred to new plates before colorimetrical measurements performed at 570 nm for the MTT test and at 630 nm for the protein determination (universal microplate reader ELx800UV; Bio-Tek Instruments Inc.).

Example 3

Cells, Plasmids and Viruses

HeLa and cultured human corneal fibroblasts (CF) cells were grown in Dulbecco's Modified Eagles Medium (DMEM; Invitrogen Corp.) supplemented with 10% fetal bovine serum (FBS), while wild-type CHO-K1 cells expressing gD receptors (nectin-1 and 3-OST-3) were grown in Ham's F-12 medium (Gibco/BRL) supplemented with 10% FBS, and penicillin and streptomycin (Gibco/BRL). Normal human dermal fibroblasts (NHDF; PromoCell, C-12300) were cultured in Quantum 333 medium (PAA, U15-813) supplemented with 1% (v/v) penicillin/streptomycin. Subcultured fibroblasts (maximum until passage 9) were seeded into 96-well microtiter plates at a seeding density of 100,000 cells/cm$^2$ in 310 μl/cm$^2$ medium. Cells were kept at 37° C. and 5% $CO_2$. The β-galactosidase expressing recombinant HSV-1 (KOS) gL86 (Shukla et al., 1999) and GFP-expressing HSV-1 (K26GFP) were provided by P. G. Spear (Northwestern University, Chicago) and P. Desai (Johns Hopkins University) (Desai and Person, 1998). The plasmids expressing nectin-1 (pBG38) was kindly provided by Dr. Spear (Northwestern University, Chicago).

Example 4

Viral Entry Assay

Viral entry assays were based on quantitation of β-galactosidase expressed from the viral genome in which β-galactosidase expression is inducible by HSV infection. Cells were transiently transfected in 6-well tissue culture dishes with plasmids expressing HSV-1 entry receptors (necitn-1 expression plasmids) using Lipofectamine 2000 at 1.5 μg DNA per well in 1 ml. At 24 h post-transfection, cells were re-plated in 96-well tissue culture dishes (2×10$^4$ cells per well) at least 16 h prior to infection. Cells were washed and exposed to serially diluted pre-incubated virus with ZnO-SCPs or 1×PBS at two fold dilutions in 50 μl PBS containing 0.1% glucose and 1% heat inactivated CS (PBS-GCS) for 6 h at 37° C. before solubilization in 100 μl PBS containing 0.5% NP-40 and the β-galactosidase substrate, o-nitro-phenyl-β-D-galactopyranoside (ONPG; ImmunoPure, PIERCE, Rockford, Ill.; 3 mg/ml). The enzymatic activity was monitored at 410 nm by spectrophotometry (BioTek Instruments Inc. ELx808 absorbance microplate reader, VT, USA).

Example 5

Mixing of Fluorescent-labeled ZnO Semiconductor Particles with GFP-tagged HSV-1

The free standing ZnO-SCPs (sea urchin and tetrapod shaped particles containing long filopodia-type of spikes) from snowflake type powder were distributed in a thin layer in a plastic Petri dish followed by irradiation with UV light at 254 nm for 30 min at room temperature. In this experiment ZnO-SCPs were stained with 10 nm rhodamine conjugated phalloidin (Invitrogen) followed by mixing with GFP-tagged HSV-1 or with 1×PBS. Images of fluorescent labeled ZnO-SCPs (either pre-treated with UV, UV+, or untreated, UV−)

mixed with GFP-tagged HSV-1 were acquired using a confocal microscope (Nikon D-Eclipse-C1) with the software EZ-C1.

Example 6

Virus-free Cell-to-cell Fusion Assay

In this experiment, the CHO-K1 cells (grown in F-12 Ham, Invitrogen) designated as "effector" cells were co-transfected with plasmids expressing four HSV-1 (KOS) glycoproteins, pPEP98 (gB), pPEP99 (gD), pPEP100 (gH) and pPEP101 (gL), along with the plasmid pT7EMCLuc that expresses firefly luciferase gene under the T7 promoter (Tiwari et al., 2004). Wild-type CHO-K1 cells express cell surface HS but lack functional gD receptors, therefore they have been transiently transfected with HSV-1 entry receptors. Wild type CHO-K1 cultured cells expressing HSV-1 entry receptor nectin-1 considered as "target" cells were co-transfected with pCAGT7 that expresses T7 RNA polymerase using chicken actin promoter and CMV enhancer. The untreated effector cells expressing pT7EMCLuc and HSV-1 essential glycoproteins and the target cells expressing gD receptors, transfected with T7 RNA polymerase, were used as the positive control, while the effector cells pre-treated with the ZnO-SCPs were used for the test. For fusion, at 18 h post transfection, the target and the effector cells were mixed together (1:1 ratio) and cocultivated in 24 well-dishes. The activation of the reporter luciferase gene as a measure of cell fusion was examined using reporter lysis Assay (Promega) at 24 h post mixing.

Example 7

HSV-1 Entry Blocking Assays with SCPs and Various Viral-strains

Clinical strains of HSV (F, G, and MP at 25 pfu/cell) were either pre-incubated with 1×PBS (−) or with ZnO-SCPs(+) at 10 μg/ml for 90 min at room temperature. After 90 min of incubation the two pools of viruses were incubated on CHO Ig8 cells that express β-galactosidase upon viral entry. The viral entry blocking was measured by the ONPG (ortho-nitrophenyl-β-D-galactopyranoside) assay.

Example 8

ZnO-SCPs/HSV-1 Assay in the Embryo Model of Zebrafish

β-galactosidase expressing HSV-1 (KOS) gL86 reporter virus at $2 \times 10^8$ pfu were pre-incubated with 1×PBS (−) or with 100 μg/ml SCPs (+) for 2 hours before infecting zebrafish embryos for 12 h. HSV-1 entry in both the groups of embryos was measured by the ONPG assay.

REFERENCES

Akhtar, J., Shukla, D., 2009. Viral entry mechanisms: cellular and viral mediators of herpes simplex virus entry. FEBS J. 276, 7228-7236. 454

Baram-Pinto, D., Shukla, S., Gedanken, A., Sarid, R., 2010. Inhibition of HSV-1 attachment, entry, and cell-to-cell spread by functionalized multivalent gold nanoparticles. Small 6(9), 1044-1050.

Beasley, D. G., Meyer, T. A., 2010. Characterization of the UVA protection provided by avobenzone, zinc oxide, and titanium dioxide in broad-spectrum sunscreen products. Am J Clin Dermatol. 11, 413-421.

Bowman, M. C., Ballard, T. E., Ackerson, C. J., Feldheim, D. L., Margolis, D. M., Melander, C., 2008. Inhibition of HIV fusion with multivalent gold nanoparticles. J Am Chem Soc. 130(22), 6896-6897.

Burgos, J. S., Ripoll-Gomez, J., Alfaro, J. M., Sastre, I., Valdivieso, F., 2008. Zebrafish as a new model for herpes simplex virus type-1 infection. Zebrafish 5, 323-333.

Corey, L., Spear, P. G., 1986. Infections with herpes simplex viruses. N. Eng. J. Med. 314, 686-691.

Dambrosi, S., Martin, M., Yim, K., Miles, B., Canas, J., Sergerie, Y., Boivin, G., 2010. Neurovirulence and latency of drug-resistant clinical herpes simplex viruses in animal models. J. Med. Virol. 82, 1000-1010.

Dean, H. J., Terhune, S., Shieh, M. T., Susmarski, N., Spear, P. G., 1994. Single amino acid substitutions in gD of herpes simplex virus 1 confer resistant to gD-mediated interference and cause cell type-dependent alterations in infectivity. Virology 199, 67-80. 474

Desai, P., Person, S., 1998. Incorporation of the green fluorescent protein into the herpes simplex virus type 1 capsid. J. Virol. 72, 7563-7568.

Hill, J. M., Ball, M. J., Neumann, D. M., Azcuy, A. M., Bhattacharjee, P. S., Bouhanik, S., Clement, C., Lukiw, W. J., Foster, T. P., Kumar, M., Kafman, H. E., Thompson, H. W., 2008. The high prevalence of herpes simplex virus type 1 DNA in human trigeminal ganglia is not a function of age or gender. J. Virol. 85, 8230-8234.

Kachynski, A. V., Kuzmin, A. N., Nyk, M., Roy, I., Prasad, P. N., 2008. Zinc Oxide Nanocrystals for Non-resonant Nonlinear Optical Microscopy in Biology and Medicine. J Phys Chem C Nanomater Interfaces. 112, 10721-10724.

Kaye, S. B., Baker, K., Bonshek, R., Maseruka, H., Grinfeld, E., Tullo, A., Easty, D. L., Hart, C. A., 2000. Human herpesviruses in the cornea. Br. J. Opthalmol. 84, 563-571.

Kong, J., Chu, S., Olmedo, M., Li, L., Yang, Z., Liu, J., 2008. Dominant ultraviolet light emissions in packed ZnO columnar homojunction diodes Appl. Phys. Lett. 93, 132113.

Lara, H. H., Ayala-Nuñez, N. V., Ixtepan-Turrent, L., Rodriguez-Padilla, C. 2010. Mode of antiviral action of silver nanoparticles against HIV-1. J. Nanobiotechnology. 20; 8:1. Liesegang, T. J., 2001. Herpes simplex virus epidemiology and ocular importance. Cornea 20, 1-13.

Liesegang, T. J., 2001. Herpes simplex virus epidemiology and ocular importance. Cornea 20, 1-13.

Lowry, O. H., Rosebrough, N. J., Fan, A. L., and Randall, R. J. (1951) J. Biol. Chem. 193, 265-275.

Montgomery Rebecca I., Warner Morgyn S., Lum Brian J., Spear Patricia G. Herpes Simplex Virus-1 Entry into Cells Mediated by a Novel Member of the TNF/NGF Receptor Family. Cell. 1996; 87(3):427-436.

Mosmann, T., 1983. Rapid colorimetric assay for cellular growth and survival: Application to proliferation and cytotoxicity assays. J. Immunological Methods 65, 55-63.

Rasmussen, J. W., Martinez, E., Louka, P., Wingett, D. G., 2010. Zinc oxide nanoparticles for selective destruction of tumor cells and potential for drug delivery applications. Expert Opin Drug Deliv. 9, 1063-1077.

Roehl, C., Sievers, J., 2005. Microglia is activated by astrocytes in trimethyltin intoxication. Toxicology and Applied Pharmacology 204, 36-45.

Schulte, E. C., Sauerbrei, A., Hoffmann, D., Zimmer, C., Hemmer, B., Mühlau, M., 2010. Acyclovir resistance in herpes simplex encephalitis. Ann Neurol. 67, 830-833.

Shukla, D., Liu, J., Blaiklock, P., Shworak, N. W., Bai, X., Esko, J. D., Cohen, G. H., Eisenberg, R. J., Rosenberg, R. D., Spear, P. G., 1999. A novel role for 3-O-sulfated heparan sulfate in herpes simplex virus 1 entry. Cell 99, 13-22.

Superti, F., Ammendolia, M. G., Marchetti, M., 2008. New advances in anti-HSV chemotherapy. Curr Med Chem. 15, 900-911.

Tallury, P., Malhotra, A., Byrne, L. M., Santra, S., 2010. Nanobioimaging and sensing of infectious diseases. Adv Drug Deliv Rev. 62(4-5):424-37.

Tiwari, V., Clement, C., Duncan, M. B., Chen, J., Liu, J., Shukla, D., 2004. A role for 3-° sulfated heparin sulfate in cell fusion induced by herpes simplex virus type 1. J. Gen. Virol. 85, 805-809.

Tiwari, V., Clement, C., Xu, D., Valyi-Nagy, T., Yue, B. Y., Liu, J., Shukla, D., 2006. Role for 3-O-sulfated heparan sulfate as the receptor for herpes simplex virus type 1 entry into primary human corneal fibroblasts. J. Virol. 80, 8970-8980.

Travan, A., Marsich, E., Donati, I., Benincasa, M., Giazzon, M., Felisari, L., Paoletti, S., 2010. Silver-polysaccharide nanocomposite antimicrobial coatings for methacrylic thermosets. Acta Biomater. [Epub ahead of print]

Vig, K., Boyoglu, S., Rangari, V., Sun, L., Singh, A., Pillai, S., Singh, S. R., 2008. Use of Nanoparticles as Therapy for Respiratory Syncytial Virus Inhibition. Nanotechnology 2008: Life Sciences, Medicine & Bio Materials—Technical Proceedings of the 2008 NSTI Nanotechnology Conference and Trade Show, Volume 2:543-546.

Whitley, R. J., Kimberlin, D. W., Roizman, B., 1998. Herpes simplex viruses. Clin. Infect. Dis. 26, 541-553.

Wu, J. M., Chen, Yi-R., 2011. Ultraviolet-Light-Assisted Formation of ZnONanowires in Ambient Air: Comparison of Photoresponsive and Photocatalytic Activities in Zinc Hydroxide. The Journal of Physical Chemistry 115 (5), pp 2235-2243.

What is claimed is:

1. A method for binding viral particles comprising contacting a viral particle comprising contacting a viral particle with a particle or particle agglomerate comprising a metal oxide semiconductor surface and a plurality of polar defect sites, wherein the surface of the surface to volume ratio of the particle or particle agglomerate is larger than that of a spherical particle of the same volume, and wherein the largest cross sectional length of the particle or particle agglomerate ranges from about 100 nm to about 30 μm, and wherein the particle or particle agglomerate does not significantly impair cell viability at concentrations up to 500 μg/ml.

2. The method of claim 1, wherein the particle or particle agglomerate has been doped to generate polar defect sites.

3. The method of claim 2, wherein the doping occurs directly before the particle or particle agglomerate is contacted with the viral particle.

4. The method of claim 1, wherein the particle or particle agglomerate comprises a mixture of at least two semiconductor compounds.

5. The method of claim 1, wherein the particle or particle agglomerate comprise zinc oxide (ZnO).

6. The method of claim 5, wherein the particle or particle agglomerate has been doped by UV-treatment to generate polar defect sites.

7. The method of claim 5, wherein the particle or particle agglomerate has been doped by heating under $H_2$-atmosphere to generate polar defect sites.

8. The method of claim 1, wherein viral particle is an enveloped viral particle.

9. The method of claim 8, in which the viral particle is a herpes simplex viral particle or a human immunodeficiency viral particle.

10. The method of claim 1, wherein the viral particle is present in a liquid, and the particle or particle agglomerate is added to the liquid.

11. The method of claim 1, wherein the viral particle is present on a surface, and the particle or particle agglomerate is present in a solution or suspension that is applied to the surface.

12. The method of claim 1, the particle or particle agglomerate is applied to a surface, and the surface is contacted by the viral particle.

13. The method of claim 1, wherein the particle or particle agglomerate is applied to a filter, and the filter is contacted by the virus particle.

14. The method of claim 13, wherein the filter is a blood filter.

15. The method of claim 13, wherein the filter is a water filter.

16. The method of claim 13, wherein the filter is an air filter.

17. The method of claim 1, wherein the particle or particle agglomerate has the shape of tetrapods, interconnected hexagonal rods, sea urchins capped with nanoscopic filopodia-like structures or a core covered by spikes.

* * * * *